United States Patent [19]

Marinello

[11] 4,193,401

[45] Mar. 18, 1980

[54] ORBITAL COMPRESSION CHAMBER FOR THE CURE OF INTERNAL WOUNDS AND INFLAMMATION OF THE OCULAR APPARATUS AND CENTRAL NERVOUS SYSTEM

[76] Inventor: Rosolino Marinello, Via Leonardo da Vinci, 4 -Mantova, Italy

[21] Appl. No.: 885,046

[22] Filed: Mar. 9, 1978

[30] Foreign Application Priority Data

Mar. 17, 1977 [IT] Italy .................... 84917 A/77

[51] Int. Cl.² .................. A61M 7/00; A61F 13/12
[52] U.S. Cl. .................... 128/260; 128/163
[58] Field of Search ............. 128/1 R, 250 A, 64, 128/76.5, 82, 97, 163, 249, 260–261, 380, 410; 2/428, 440, 452

[56] References Cited

U.S. PATENT DOCUMENTS

| | | | |
|---|---|---|---|
| 2,494,393 | 1/1950 | Lamson | 128/64 |
| 2,555,636 | 6/1951 | Felts et al. | 128/25 A |
| 2,690,173 | 9/1954 | Seeger et al. | 128/25 A |
| 3,171,410 | 3/1965 | Towle, Jr. et al. | 128/155 |
| 3,339,206 | 9/1967 | Daley | 128/163 |
| 3,908,645 | 9/1975 | Sandvig | 128/97 |
| 3,952,735 | 4/1976 | Wirtschafter et al. | 128/163 |

FOREIGN PATENT DOCUMENTS 25652 11/1910 United Kingdom ............. 128/163

*Primary Examiner*—Robert W. Michell
*Assistant Examiner*—C. F. Rosenbaum
*Attorney, Agent, or Firm*—Beveridge, DeGrandi, Kline and Lunsford

[57] ABSTRACT

A hollow spectacles framework provided at the usual lens location with a pair of membranes to form a pair of pressure chambers connectible with a pressure source. The framework is mounted so that one pressure chamber covers each eye. A medicament-impregnated dressing is mounted on the membrane facing the eye, so that pressurization of the pressure chamber squeezes medicaments out of the dressing and into the ocular organ.

6 Claims, 6 Drawing Figures

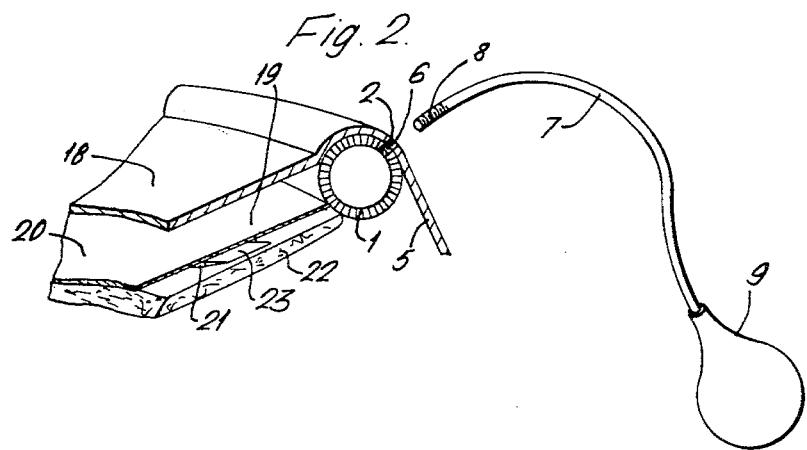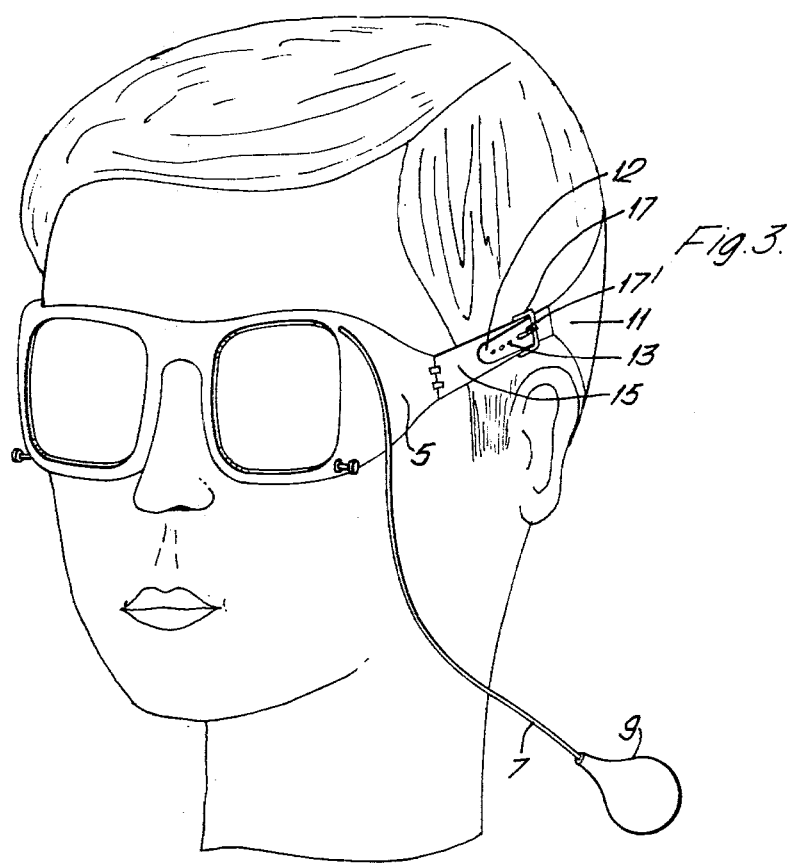

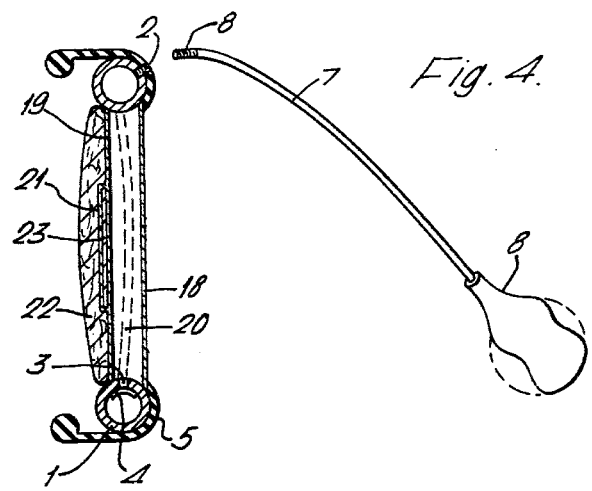
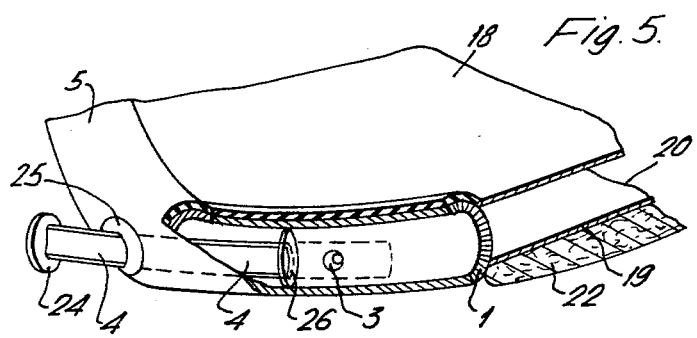
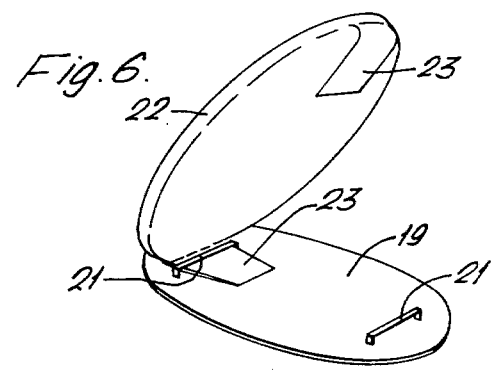

ORBITAL COMPRESSION CHAMBER FOR THE CURE OF INTERNAL WOUNDS AND INFLAMMATION OF THE OCULAR APPARATUS AND CENTRAL NERVOUS SYSTEM

SUMMARY OF THE INVENTION

The above invention concerns an apparatus applicable to the external part of the orbital cavity in order to keep different medicaments held against it at any given pressure.

It can be substantially defined as a mechanism having the function of being able to keep firmly held against the orbital cavity, at any given pressure, a dressing soaked in medicaments, in a way that the pressure be exerted on the zone where the pain is located. The pressure is to be of an intensity necessary to obtain a curative effect.

The apparatus includes a skeleton spectacle frame made of plastic or similar material, with two circles of a greater thickness than used on normal glasses and provided on the outside with a rigid margin rounded at the edges. When set in place against the cheeks and the eyebrows, it covers the surrounding zone.

The framework of the two circles is formed of a hollow tube. At the far end of the hollow tube there is an aperture into which a small rubber tube is screwed. This tube has at its end a small pump which pumps air into the hollow tube of the glasses through the rubber tube.

On the inside of the hollow tube, there are two holes both formed in the central part of each circle. These holes may be closed from the outside by means of a small lever.

The framework of the glasses does not have arms. In place of them a band, made of a resistant fabric has been substituted. Attached to the far end of the framework by means of a hinge, this fabric band has the function of winding round the nape of the neck and tying up on the other side of the frame. It is necessary that the fabric band be sewn on to a small leather belt which has a row of holes in it. At the opposite end of the glasses framework also attached by a hinge, there is a small belt which finishes in a buckle, and into which the leather end of the band, provided with holes, is inserted. In all this ensures that the glasses framework be kept firmly in place without any possibility of shifting.

On the outside part of the glasses framework in place of the lenses, two rigid membranes are imbedded and opposite these, on the inside, two elastic membranes, also firmly fastened on to the framework of the glasses form the two internal walls. Between the outside and inside membranes there remains an empty space closed on the outside by the four membranes of the glasses framework.

The empty space is in communication with the hollow tube by means of the corresponding holes in the two circles. This existant empty space between the two pairs of membranes makes up the compression chamber.

On the outside walls of the elastic membranes and the two opposite outside ends, two loops, made of an elastic material, are attached. Through these a dressing, impregnated with medicaments is inserted and applied to the orbital cavity.

BRIEF DESCRIPTION OF THE DRAWINGS

For greater clarification, a detailed description of the apparatus follows with reference to the illustrations which are attached to the design plates:

FIG. 2 shows a sectional part of the apparatus;

FIG. 3 shows the apparatus in place;

FIGS. 4 and 5 show the apparatus in action, in sectional views; and

FIG. 6 shows the tongues inserted into the loops of the elastic membrane.

DETAILED DESCRIPTION

Figure 1:
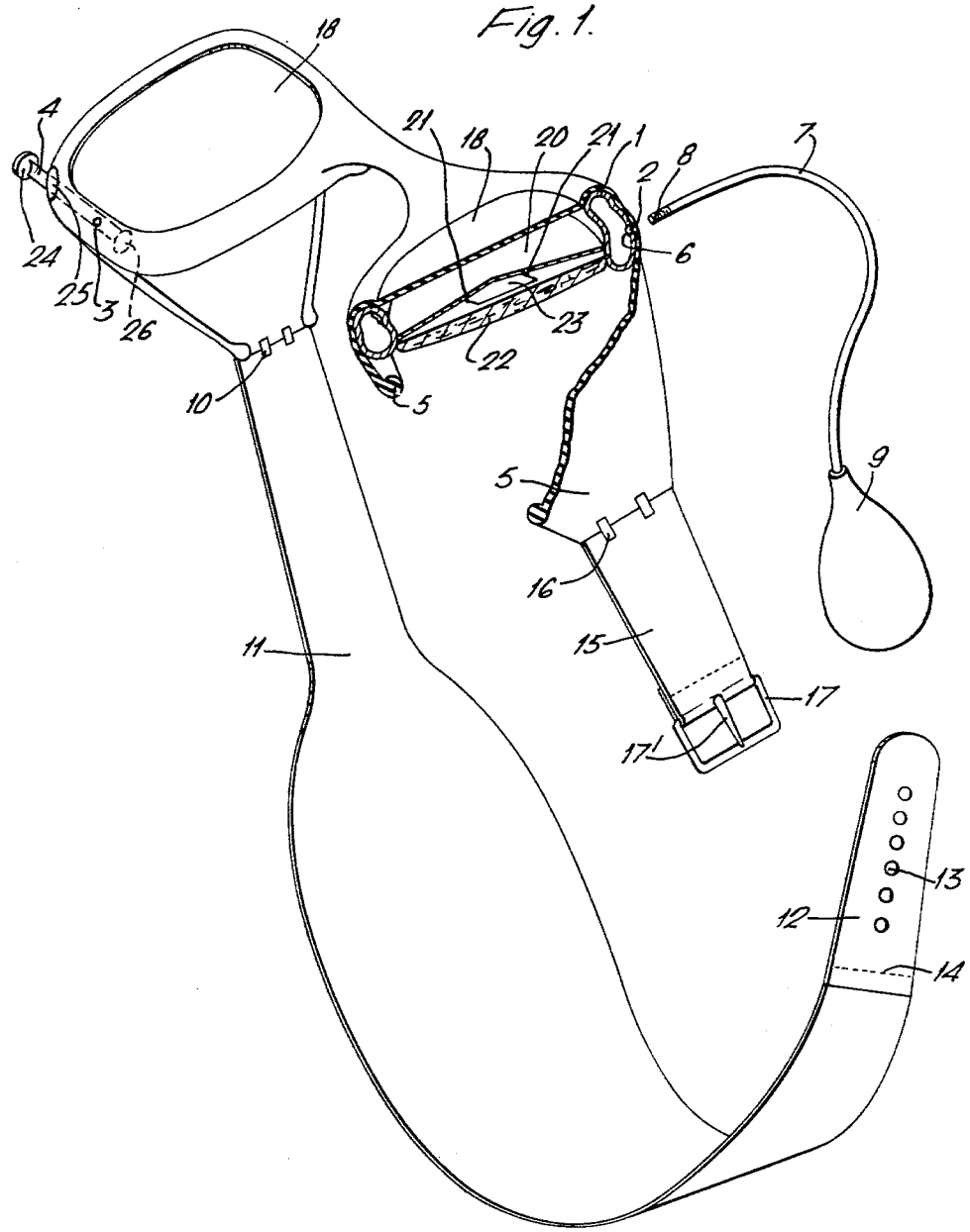
FIG. 1 shows the appliance seen in perspective and partially sectioned.

The importance of the apparatus in question as seen in FIG. 1, is the form of the skeleton framework of the glasses in which the two circles are formed from a hollow tube (1) communicating with the outside by a hole (2).

In the center of the two circles in the middle inside part, a hole (3) has been made which, by means of a small lever (4) inserted into the hollow tube, may be closed.

On the outside of each of the two circles of the glasses framework there is a border of rigid plastic material (5) rounded at the edges which, when set in place against the cheeks and eyebrows, covers the entire orbital area.

The hole (2) in the glasses framework (1) is provided with a lead-screw. A small rubber tube (7) provided at one end with a thread (8) is screwed into the lead-screw (6) of the glasses framework and has at its other end a small pump (9) provided with a valve and having the function of pumping air through the small rubber tube (7) into the hollow frame tube (1).

At one end of the glasses framework (1) there is a band of resistant cloth material (11) attached by a hinge (10). At the far end of this band there is a small leather belt (12) provided with holes (13). The said leather belt is sewn (14) to the material band.

At the opposite end of the glasses framework there is another small leather belt (15) attached to the glasses framework by another hinge (16) and which in its turn ends with a buckle (17) and hook (17').

On the two outside rings of the glasses framework two membranes, made of rigid material (18) are firmly attached while on the opposite inside part there are two membranes (19) made of an elastic material.

The two empty spaces formed inside the four membranes, two rigid and two elastic, and by the two circles of the glasses make up the compression chambers (20).

On the outside walls of the two elastic membranes (19) and at the opposite ends of the same are two fixed loops (21) which perform the task of retaining the dressing soaked in medicaments and to apply it against the orbital cavity.

FIGS. 2 and 3 show the method of applying the device in order to permit it to function properly.

It is necessary to affix the dressing (22), impregnated with medicaments, to the elastic membrane (19) making the small tongues (23) pass through the loops (21) to be thus inserted, as seen in FIG. 6.

In the case of medication to one orbital cavity only, the dressing will be fitted into the loops (21) of only one of the two elastic membranes. In the case of both cavities requiring medication the two dressings are then fixed into the loops (21) of both the elastic membranes.

The device is then rested on the cheeks and against the eyebrows in a way that the edges (5), with their outside borders rounded, cover the whole area surrounding the orbital cavity.

One then proceeds by taking the free end of the fabric band (11) attached to its holed (13) leather belt (12) and wrapping it around the nape of the neck, inserting it into the buckle (17) of the other leather belt (15) firmly stopping it with the hook (17') provided, thus firmly securing the fabric band to the head of the patient.

FIGS. 4 and 5 show the apparatus in action.

In particular FIG. 5 shows how the small lever (4) works.

This, inserted into the hollow tube (1) through the slot made in the rubber cap (25) blocks the said slot by means of plugs (24 & 26) according to whether the hole (3) is to be closed or left open.

Looking at the two illustrations we can see that the air is pushed in by the pump (9) through the small rubber tube (7) and the hole (2) into the hollow tube (1) and, from there through the middle holes (3), enters in to the compression chamber (20) thus exerting pressure against its inside walls.

As the outside walls are rigid the pressure is concentrated against the two inside elastic membranes (19) which, under the thrust, stretch to inflate, transmitting pressure against the dressing, FIG. 6, which in its turn presses against the orbital cavity.

As the air enters and fills the compression chamber (20) the dressing, placed between the membrane and the orbital wall, will therefore have a pressure exerted against the orbital cavity.

FIG. 6 shows the dressing (22) inserted with the tongues (23) in the loops (21) of the membrane (19).

From the preceeding it appears evident that the apparatus has a static function i.e. to keep the dressing against the orbital cavity, and the other dynamic i.e. to press the said dressing against the orbital cavity in order to concentrate the medicaments and inject them as near as possible to the injured or inflamed part.

The apparatus can be used for the cure of internal injuries or inflammation of the eye and the central nervous system.

The case in which an injury or inflammation is limited to one eye only, the manipulation of the lever (4) on the inside holes (3) corresponding to the compression chamber (20) which is to be kept inert, will obturate them so that the influx of air is concentrated towards the compression chamber which is to be activated.

It is not intended that the invention be limited only to the forms described above and that perfection and variants of the model may be produced, without however, detracting from the basic design of which the essential characteristics are summarized in the following.

I claim:

1. An appliance for the cure of internal injuries, wounds, or inflammation to the ocular organs and the central nervous system of a patient comprising:
   (a) a hollow spectacles framework provided with an ocular opening having a pair of membranes thereacross, one of said membranes being flexible and facing the ocular side of said framework, said membranes and said framework defining a pressure chamber communicating with the interior of said hollow spectacles framework;
   (b) means for connecting a source of pressure to said hollow framework to provide pressure to the pressure chamber;
   (c) a dressing impregnated with a medicament affixed to said flexible membrane on its ocular side; and
   (d) a mounting means for securing said framework against the orbital cavity of said patient.

2. An appliance as claimed in claim 1 wherein said hollow spectacles framework is provided with two ocular openings, each of said ocular openings having a pair of membranes thereacross, one of each of said pair of membranes being flexible and facing the ocular side of said framework, said membranes and said framework defining said pressure chamber in each of said ocular openings, and controllable valve means between the pressure chambers and the interior of said hollow spectacles framework.

3. An appliance as claimed in claim 2 wherein said controllable valve means comprises
   a first pair of openings in said hollow framework, each of said pair of openings communicating with one of said pressure chambers,
   a second pair of openings in said hollow framework,
   a pair of levers, each of said levers extending through one of said second pair of openings and said hollow framework, each of said pair of levers movable from a first position covering one of said first pair of openings to a second position uncovering said first opening,
   whereby each of said pressure chambers may be isolated from said pressure source.

4. An appliance as claimed in claim 1 including a tube and a pump providing the pressure source for pumping fluid into said tube, said tube communicating with said hollow spectacles framework.

5. An appliance as claimed in any of claims 1, 3 or 4 wherein said mounting means comprises a band of resistant material having one end hingedly connected to one temple of said framework and the other end provided with a perforate belt,
   a buckle means hingedly connected to the other temple of said framework,
   whereby said resistant material may be wound around the nape of the neck of the patient and the belt may be secured in the buckle.

6. A method of curing internal injuries, wounds, or inflammation to the ocular organ and the central nervous system comprising the steps of:
   providing an apparatus for securing a medicament-impregnated dressing on the exterior of a pressurizable chamber, said apparatus including a hollow spectacles framework provided with an ocular opening a hollow spectacles framework provided with an ocular opening having a pair of membranes thereacross, one of said membranes being flexible and facing the ocular side of said framework, said membranes and said framework defining a pressure chamber communicating with the interior of said hollow spectacles framework, means for connecting a source of pressure to said hollow framework to provide pressure to the pressure chamber, and a mounting means for securing said framework against the orbital cavity of said patient,
   situating said apparatus against said ocular organ with said dressing facing and exposed to said ocular organ,
   pressurizing said pressurable chamber to press said medicaments out of said dressing and inject them as deeply as possible towards the injury, wound, or inflammation.

* * * * *